(12) United States Patent
DuBois et al.

(10) Patent No.: US 8,687,194 B2
(45) Date of Patent: Apr. 1, 2014

(54) SMALL PARTICLE SENSOR

(76) Inventors: Jerry DuBois, West Des Moines, IA (US); Scott James Bohemann, Des Moines, IA (US)

( * ) Notice: Subject to any disclaimer, the term of this patent is extended or adjusted under 35 U.S.C. 154(b) by 249 days.

(21) Appl. No.: 13/347,037

(22) Filed: Jan. 10, 2012

(65) Prior Publication Data
US 2013/0176569 A1 Jul. 11, 2013

(51) Int. Cl.
*G01N 21/00* (2006.01)
(52) U.S. Cl.
USPC .......................................................... 356/432
(58) Field of Classification Search
None
See application file for complete search history.

(56) References Cited

U.S. PATENT DOCUMENTS

| | | |
|---|---|---|
| 3,462,845 A | 8/1969 | Matthews |
| 4,635,474 A | 1/1987 | Blackwood |
| 6,078,635 A | 6/2000 | DuBois |

*Primary Examiner* — Gregory J Toatley
*Assistant Examiner* — Amanda Merlino
(74) *Attorney, Agent, or Firm* — Zarley Law Firm, P.L.C.

(57) ABSTRACT

A sensor having a housing with a first member connected to a second member to form a circular central opening. A plurality of photoelectric transmitters and receivers are placed between the first member and the second member such that each receiver is within a liner-of-sight of each transmitter across the central opening and the signals sent between the receivers and transmitters fills an area of detection.

7 Claims, 4 Drawing Sheets

SMALL PARTICLE SENSOR

BACKGROUND OF THE INVENTION

This invention is directed toward a sensor and more particularly a sensor for small particles.

Sensors are well known in the art and are used for a number of applications including, but not limited to, detecting pills and agricultural seeds. In many of these applications, obtaining an accurate count of the particle is important. Existing sensors, because of their structure, are unable to detect small or micro particles with great accuracy within an area of detection. Accordingly, a need exists in the art for a device that addresses these deficiencies.

Therefore, an objective of the present invention is to provide a device that senses small particles with accuracy.

This and other objectives will be apparent to one of ordinary skill in the art based on the following written description, drawings and claims.

SUMMARY OF THE INVENTION

A sensor having a housing with a first member connected to a second member to form a circular central opening. A plurality of photoelectric transmitters and receivers are placed between the first member and the second member such that each receiver is within a line-of-sight of each transmitter across the central opening.

DETAILED DESCRIPTION OF THE PREFERRED EMBODIMENTS

Figure 1:
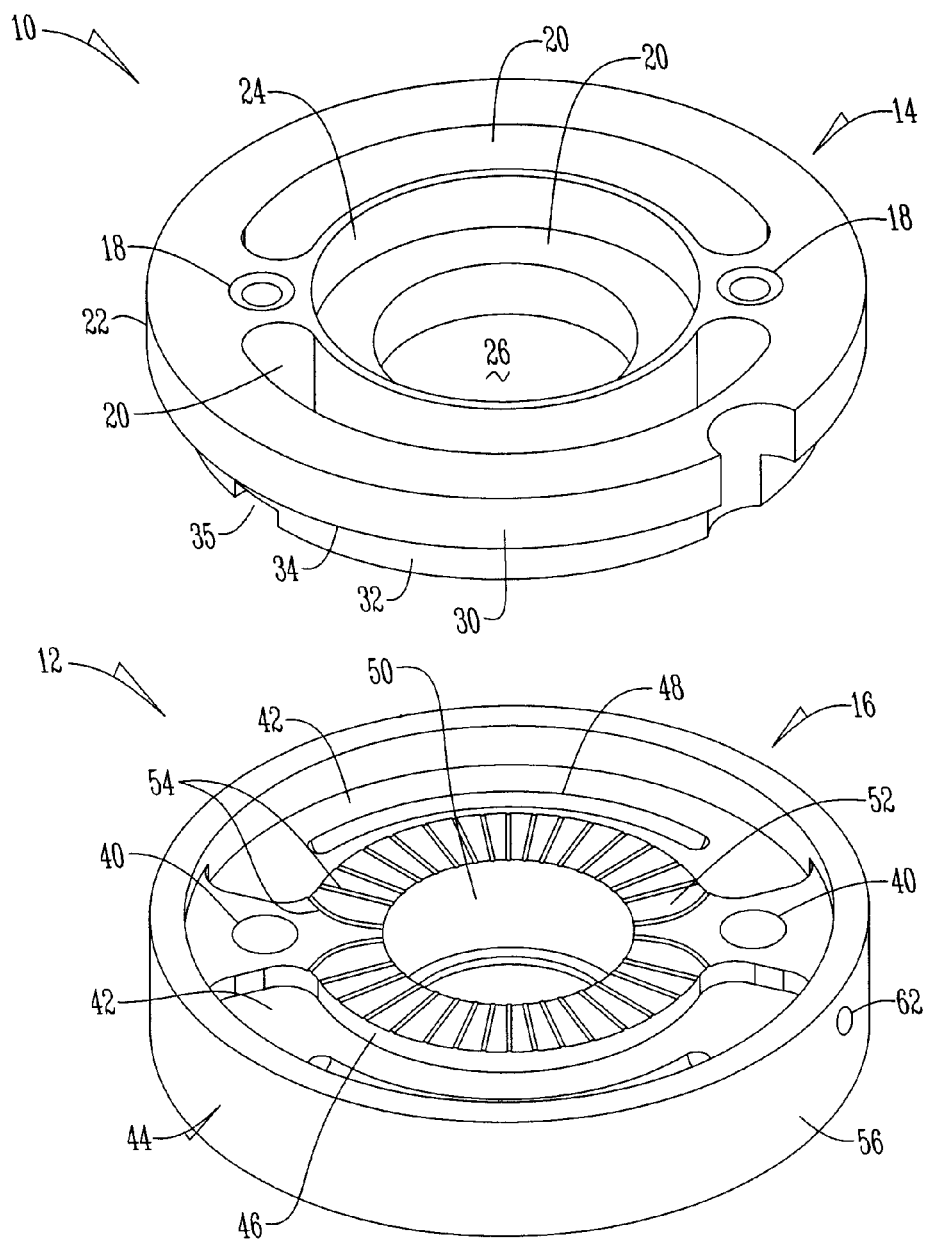
FIG. 1 is an exploded perspective view of a sensor.
Figure 2:
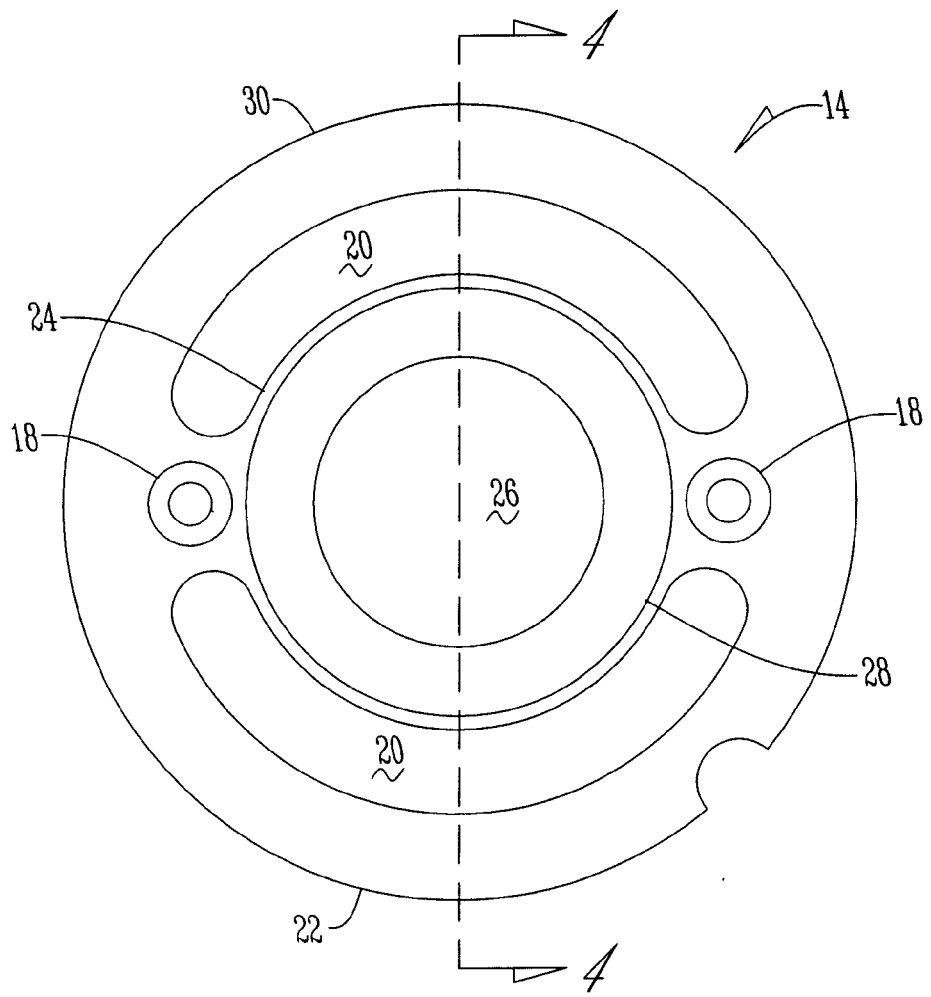
FIG. 2 is a top plan view of a first member of a sensor.
Figure 3:
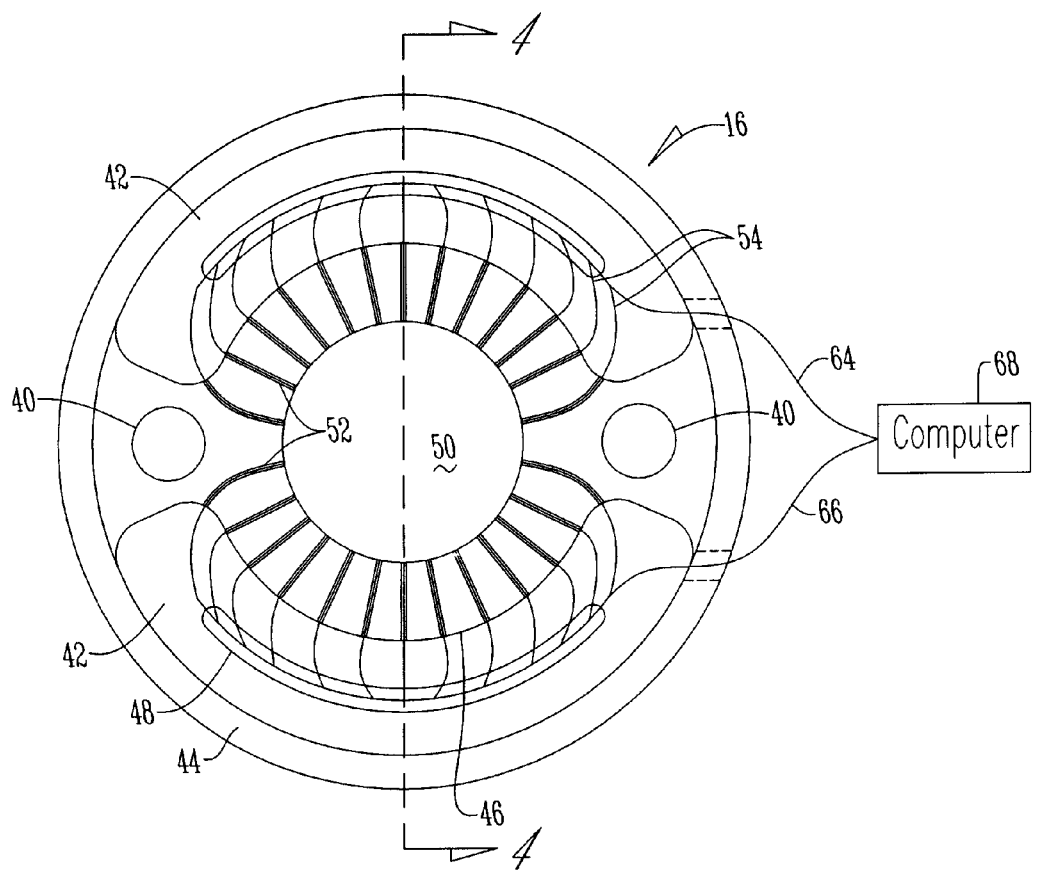
FIG. 3 is a top plan view of a second member of a sensor.
Figure 4:
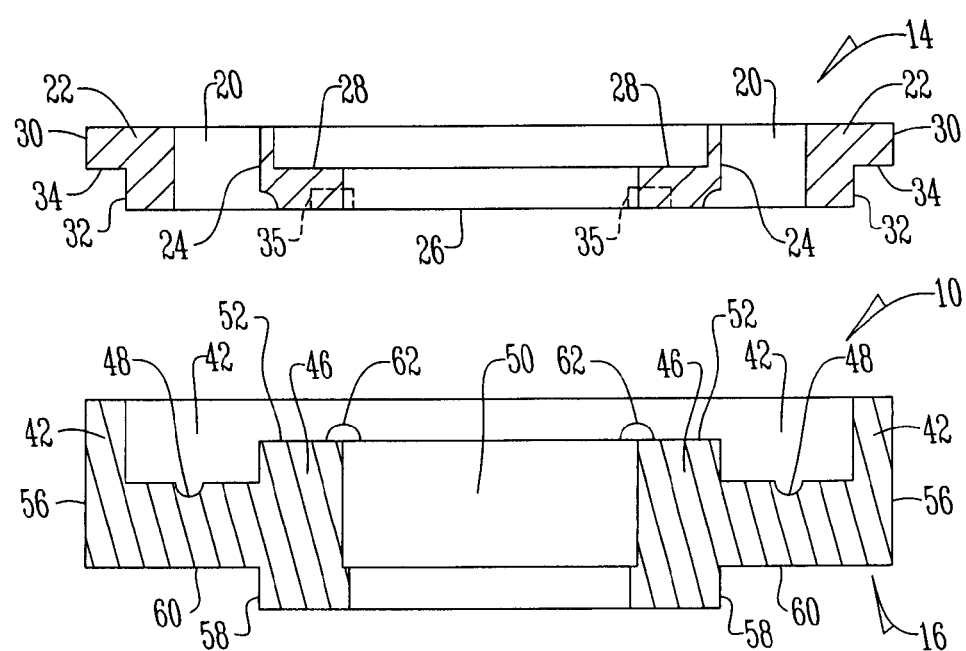
FIG. 4 is a side view of a sensor.

Referring to the Figures, the sensor 10 has a housing 12 that is formed by the connection of a first and second member 14, 16. The housing 12 is of any shape and structure but preferably is circular. The first member 14 has a pair of threaded bores 18 that are opposite to one another. Extending between the bores 18 along the outer periphery of the first member 14 are a pair of openings 20 that are opposite to one another. The openings 20 form an outer and inner wall 22, 24. In the circular embodiment the openings 20 are arcuate.

Inside the inner wall 24 is a central opening 26 that has a diameter less than the inner wall 24 such that a shelf 28 is formed between the central opening 26 and the inner wall 24. The outer wall 22 has a primary outer edge 30 and a secondary outer edge 32 wherein the secondary edge 32 has a diameter less than the diameter of the primary edge 30 to form a shoulder 34. The shoulder 34 has two slots 35 that permit access to openings 20. Likewise, preferably the inner wall 24 has a primary outer edge 36 that tapers inwardly to a secondary edge 38 of a smaller diameter.

The second member 16 has a pair of threaded bores 40 that are opposite to one another and are positioned to align with bores 18 of the first member 14. Extending between bores 40 along the outer periphery of the second member 16 are a pair of slots 42 that are opposite to one another and positioned to align with openings 20 of the first member 14. The slots 42 form an outer wall 44 and inner wall 46 that are in general alignment with the outer and inner wall 22, 24 of the first member 14. Disposed within the slots 42 are longitudinally extending grooves 48.

Inside the inner wall 46 is a central opening 50 that is positioned to align with the central opening 26 of the first member 14. The aligned central openings create an area of detection. The central opening 50 has a diameter that is less than the diameter of the inner wall 46 to form a shelf 52 that is positioned to align with and engage with shelf 28 of the first member 14. Extending from the inner wall 46 to the central opening 50 are a plurality of grooves 54 that are cut into the shelf 52. The outer wall 44 has a primary edge 56 and a secondary edge 58. The secondary edge 58 has a diameter less than the diameter of the primary edge 56 which forms a shoulder 60. On the primary edge 56 are a pair of ports 62 that are positioned to align with slots 35 on the first member 14.

To assemble the sensor 10, a plurality of photoelectric transmitters 64 are inserted through one port 62 and into slot 42. From there each transmitter is placed in a groove 54 of shelf 52. The longitudinally extending grooves 48 within slot 42 facilitate and grasp each transmitter 64 during assembly. Next, a plurality of photoelectric receivers 66 are inserted through the other port 62 and into the other slot 42. Each receiver 66 is then placed within a groove 54 of shelf 52 such that each receiver 66 is located within the line-of-sight of a corresponding transmitter 64.

Once the transmitters 64 and receivers 66 are in place the first member 14 is matingly and frictionally inserted within the second member 16. More specifically the secondary edge 32 of the first member 14 is inserted within the outer wall 44 of the second member 16 such that the transmitters 64 and receivers are trapped within grooves 54 as shelf 52 engages shelf 28. The first member 14 is also inserted within the second member 16 such that bores 18 align with bores 40 and slots 35 align with ports 62. To complete the assembly screws are inserted through bores 18 and 40 and a sealant material is placed into openings 20 and slots 42.

In operation small particles flow through central openings 26 and 50. When a small particle at least partially blocks a light beam from a transmitter 64 to a receiver 66 to change the intensity of the beam within the area of detection, a signal is sent to a computer 68 causing the computer to detect the small particle.

Accordingly, a sensor has been disclosed that senses small particles accurately and at the very least meets all the stated objectives.

What is claimed is:

1. A sensor, comprising
a housing formed of a first member connected to a second member;
a plurality of photoelectric transmitters and receivers that are inserted through ports and into slots in the second member wherein each transmitter and each receiver are placed in a groove disposed in a shelf of the second member such that each receiver is in a line-of-sight of each transmitter; and
the first member has a shelf that engages the shelf of the second member to trap the transmitters and receivers within the grooves.

2. The sensor of claim 1 wherein the housing is circular.

3. The sensor of claim 1 wherein each slot has a longitudinally extending groove.

4. The sensor of claim 1 wherein the first member has an outer wall with a secondary edge that fits within an outer wall of the second member.

5. A sensor, comprising a housing having a first member connected to a second member;

the first member having a shelf and a central opening;

the second member having a pair of slots, a central opening and a shelf between the slots and the central opening, and a plurality of photoelectric transmitters and receivers that are inserted into the slots and are held between the shelf of the first member and the shelf of the second member such that each receiver is in a line-of-sight with each transmitter.

6. The sensor of claim 5 wherein the signals between the receivers and transmitters fill an area of detection.

7. The sensor of claim 1 wherein the signals between the receivers and transmitters fill an area of detection.

\* \* \* \* \*